United States Patent
Kopetzki et al.

(10) Patent No.: US 6,277,618 B1
(45) Date of Patent: Aug. 21, 2001

(54) RECOMBINANT BLOOD-COAGULATION PROTEASES

(75) Inventors: Erhard Kopetzki; Karl-Peter Hopfner, both of Deutschland (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/202,101

(22) PCT Filed: Jun. 11, 1997

(86) PCT No.: PCT/EP97/03027

§ 371 Date: Apr. 12, 1999

§ 102(e) Date: Apr. 12, 1999

(87) PCT Pub. No.: WO97/47737

PCT Pub. Date: Dec. 18, 1997

(30) Foreign Application Priority Data

Jun. 6, 1996 (DE) .................................................. 96110959
Jun. 11, 1996 (DE) .................................................. 96109288
Jun. 22, 1996 (DE) .................................................. 96110109

(51) Int. Cl.[7] ..................................................... C12N 9/50
(52) U.S. Cl. ............................... 435/219; 435/4; 435/23; 435/24; 435/183; 435/218; 435/219; 435/252.3; 435/320.1; 435/226; 530/380; 530/381; 530/383; 530/384
(58) Field of Search .................................... 435/4, 23, 24, 435/183, 218, 219, 252.3, 320.1, 226, 69.6, 69.7; 530/380, 381, 383, 384

(56) References Cited

U.S. PATENT DOCUMENTS 5,585,253 * 12/1996 Doi et al. ......................... 435/172.3

OTHER PUBLICATIONS

Choo et al. Molecular cloning of the genes for human anti–haemophilic factor IX. Nature, 1982, vol. 299:178–180, 1982.*
Lin et al. Expression and characterization of human factor IX and factor IX–factor X chimeras in mouse C127 cells. J. Biol. Chem. 1990, vol. 265:144–150, 1990.*
Hertzberg et al. Construction, expression and characterization of a chimera of factor IX and factor X. J. biol. Chem. 1992, vol. 267:14759–14766.*
Strongin et al. J. gen Microbiol., 1979, vol. 110(2):442–451. (Abstract only), 1979.*

* cited by examiner

Primary Examiner—Rebecca E. Prouty
Assistant Examiner—Manjunath N. Rao
(74) Attorney, Agent, or Firm—Fulbright & Laworski, LLP

(57) ABSTRACT

The invention relates to a non-glycosylated protein with enzymatic and serin protease activity, the zymogenous form thereof comprising the following domains of a protease of the factor IX family: (a) a catalytic domain, N-terminal bonded with (b) a zymogenous activation domain, N terminal bonded with (c) a EGF1 and/or EGF2 domain. Said protein can be used in a same way as the natural serine proteases of the factor IX family.

17 Claims, 9 Drawing Sheets

| | | | | | | | | | | | | | | | |
|---|---|---|---|---|---|---|---|---|---|---|---|---|---|---|---|
| CTG | CTC | GGG | GAA | AGT | CTG | TTC | ATC | CGC | AGG | GAG | CAG | GCC | AAC | AAC | ATC | 48 |
| Leu | Leu | Gly | Glu | Ser | Leu | Phe | Ile | Arg | Arg | Glu | Gln | Ala | Asn | Asn | Ile | 16 |
| CTG | GCG | AGG | GTC | ACG | AGG | GCC | AAT | TCC | TTT | CTT | GAA | GAG | ATG | AAG | AAA | 96 |
| Leu | Ala | Arg | Val | Thr | Arg | Ala | Asn | Ser | Phe | Leu | Glu | Glu | Met | Lys | Lys | 32 |
| GGA | CAC | CTC | GPA | AGA | GAG | TGC | ATG | GAA | GAG | ACC | TGC | TCA | TAC | GAA | GAG | 144 |
| Gly | His | Leu | Arg | Arg | Glu | Cys | Met | Glu | Glu | Thr | Cys | Ser | Tyr | Glu | Glu | 48 |
| GCC | CGC | GAG | GTC | TTT | GAG | GAC | AGC | GAC | AAG | ACG | AAT | GAA | TTC | TGG | AAT | 192 |
| Ala | Arg | Glu | Val | Phe | Glu | Asp | Ser | Asp | Lys | Thr | Asn | Glu | Phe | Trp | Asn | 64 |
| AAA | TAC | AAA | GAT | GGC | GAC | CAG | TGT | GAG | ACC | AGT | CCT | TGC | CAG | AAC | CAG | 240 |
| Lys | Tyr | Lys | Asp | Gly | Asp | Gln | Cys | Glu | Thr | Ser | Pro | Cys | Gln | Asn | Gln | 80 |
| GGC | AAA | TGT | AAA | GAC | GGC | CTC | GGC | GAA | TAC | ACC | TGC | ACC | TGT | TTA | GAA | 288 |
| Gly | Lys | Cys | Lys | Asp | Gly | Leu | Gly | Glu | Tyr | Thr | Cys | Thr | Cys | Leu | Glu | 96 |
| GGA | TTC | GAA | GGC | AAA | AAC | TGT | GAA | TTA | TTC | ACA | CGG | AAG | CTC | TGC | AGC | 336 |
| Gly | Phe | Glu | Gly | Lys | Asn | Cys | Glu | Leu | Phe | Thr | Arg | Lys | Leu | Cys | Ser | 112 |
| | | | | | | | | | | |108 FX-EGF2 ->| | | | | |
| CTG | GAC | AAC | GGG | GAC | TGT | GAC | CAG | TTC | TGC | CAC | GAG | GAA | CAG | AAC | TCT | 384 |
| Leu | Asp | Asn | Gly | Asp | Cys | Asp | Gln | Phe | Cys | His | Glu | Glu | Gln | Asn | Ser | 128 |
| GTG | GTG | TGC | TCC | TGC | GCC | CGC | GGG | TAC | ACC | CTG | GCT | GAC | AAC | GGC | AAG | 432 |
| Val | Val | Cys | Ser | Cys | Ala | Arg | Gly | Tyr | Thr | Leu | Ala | Asp | Asn | Gly | Lys | 144 |
| GCC | TGC | ATT | CCC | ACA | GGG | CCC | TAC | CCC | TGT | GGG | AAA | CAG | ACC | CTG | GAA | 480 |
| Ala | Cys | Ile | Pro | Thr | Gly | Pro | Tyr | Pro | Cys | Gly | Lys | Gln | Thr | Leu | Glu | 160 |
| | | | | | | | | |154 FX-DEGF2 ->| | | | | | |

FIG. 3A

```
CGC AGG AAG AGG TCA GTG GCC CAG GCC ACC AGC AGC AGC GGG GAG GCC    528
Arg Arg Lys Arg Ser Val Ala Gln Ala Thr Ser Ser Ser Gly Glu Ala   176
              |166 FX-AP ->

CCT GAC AGC ATC ACA TGG AAG CCA TAT GAT GCA GCC GAC CTG GAC CCC    576
Pro Asp Ser Ile Thr Trp Lys Pro Tyr Asp Ala Ala Asp Leu Asp Pro   192

ACC GAG AAC CCC TTC GAC CTG CTT GAC TTC AAC CAG CAG ACG CAG CCT GAG    624
Thr Glu Asn Pro Phe Asp Leu Leu Asp Phe Asn Gln Gln Thr Gln Pro Glu   208

AGG GGC GAC AAC CTC ACC AGG ATC GTG GGA GGC CAG GAA TGC AAG            672
Arg Gly Asp Asn Leu Thr Arg Ile Val Gly Gly Gln Glu Cys Lys          224
                              |217 FX-CD ->

GAC GGG GAG TGT CCC TGG CAG GCC CTG CTC ATC AAT GAG GAA AAC GAG    720
Asp Gly Glu Cys Pro Trp Gln Ala Leu Leu Ile Asn Glu Glu Asn Glu   240

GGT TTC TGT GGA ACC ATT CTG AGC GAG TTC TAC ATC CTA ACG GCA        768
Gly Phe Cys Gly Thr Ile Leu Ser Glu Phe Tyr Ile Leu Thr Ala       256

GCC TGT CTC TAC CAA GCC AAG AGA TTC GAA GGG GAC CGG AAC ACG        816
Ala Cys Leu Tyr Gln Ala Lys Arg Phe Glu Gly Asp Arg Asn Thr       272

GAG CAG GAG GGT GAG GCG GTG CAC GAG GTG GAG GTG GTC ATC            864
Glu Gln Glu Gly Glu Ala Val His Glu Val Glu Val Val Ile          288

AAG CAC AAC CGG TTC ACA AAG GAG ACC TAT CAC TTC GAC ATC GCC GTG    912
Lys His Asn Arg Phe Thr Lys Glu Thr Tyr His Phe Asp Ile Ala Val  304

CTC CGG CTC AAG ACC CCC ATC ACC TTC CGC ATG AAC GTG GCG CCT GCC    960
Leu Arg Leu Lys Thr Pro Ile Thr Phe Arg Met Asn Val Ala Pro Ala  320
```

FIG. 3B

```
TGC CTC CCC GAC CGT GAC TGG GCC GAG TCC ACG CTG ATG ACG CAG AAG    1008
Cys Leu Pro Asp Arg Asp Trp Ala Glu Ser Thr Leu Met Thr Gln Lys     336

ACG GGG ATT GTG AGC GGC TTC GGG CGC ACC CAC GAG AAG GGC CGG CAG    1056
Thr Gly Ile Val Ser Gly Phe Gly Arg Thr His Glu Lys Gly Arg Gln     353

TCC ACC AGG CTC AAG ATG CTG GAG GTG CCC TAC GTG GAC CGC AAC AGC    1104
Ser Thr Arg Leu Lys Met Leu Glu Val Pro Tyr Val Asp Arg Asn Ser     368

TGC AAG CTC TCC AGC AGC TTC ATC ATC GAG AAC CAG ATG TTC TGT GCC    1152
Cys Lys Leu Ser Ser Ser Phe Ile Ile Glu Asn Gln Met Phe Cys Ala     384

GGC TAC GAC AAG CAG GAT GCC TGC CAG GGG GAC AGC GGG GGC            1200
Gly Tyr Asp Lys Gln Glu Asp Ala Cys Gln Gly Asp Ser Gly Gly         400

CCG CAC GTC ACC CGC TTC AAG GAC TAC TTC GTG ACA GGC ATC GTC        1248
Pro His Val Thr Arg Phe Lys Asp Thr Tyr Phe Val Thr Gly Ile Val     416

AGC TGG GGA GAG GGC TGT GCC CGT AAG GGG AAG TAC GGG ATC TAC ACC    1296
Ser Trp Gly Glu Gly Cys Ala Arg Lys Gly Lys Tyr Gly Ile Tyr Thr     432

AAG GTC ACC GCC TTC CTC AAG TGG ATC GAC AGG TCC ATG AAA ACC AGG    1344
Lys Val Thr Ala Phe Leu Lys Trp Ile Asp Arg Ser Met Lys Thr Arg     448

GGC TTG CCC AAG GCC AGC CAT GCC CCG GAG GTC ATA ACG TCC TCT        1392
Gly Leu Pro Lys Ala Ser His Ala Pro Glu Val Ile Thr Ser Ser         464
                    <- 454|

CCA TTA AAG TGA                                                    1404
Pro Leu Lys End                                                     467
```

FIG. 3C

| | | | | | | | | |
|---|---|---|---|---|---|---|---|---|
| ATG | CAG | CGC | GTG | AAC | ATG | ATC | ATG | GCA | GAA | TCA | CCA | GGC | CTC | ATC | ACC | 6 |
| Met | Gln | Arg | Val | Asn | Met | Ile | Met | Ala | Glu | Ser | Pro | Gly | Leu | Ile | Thr | 2 |
| ATC | TGC | CTT | TTA | GGA | TAT | CTA | CTC | AGT | GCT | GAA | TGT | ACA | GTT | TTT | CTT | 54 |
| Ile | Cys | Leu | Leu | Gly | Tyr | Leu | Leu | Ser | Ala | Glu | Cys | Thr | Val | Phe | Leu | 18 |
| | | | | | | | | | | | | | | | +1 | |
| GAT | CAT | GAA | AAC | GCC | AAC | AAA | ATT | CTG | AAT | CGG | CCA | AAG | AGG | TAT | AAT | 102 |
| Asp | His | Glu | Asn | Ala | Asn | Lys | Ile | Leu | Asn | Arg | Pro | Lys | Arg | Tyr | Asn | 34 |
| | | | | | | | | | | | | | | | +1 | |
| TCA | GGT | AAA | TTG | GAA | GAG | TTT | GTT | CAA | GGG | AAC | CTT | GAG | AGA | GAA | TGT | 150 |
| Ser | Gly | Lys | Leu | Glu | Glu | Phe | Val | Gln | Gly | Asn | Leu | Glu | Arg | Glu | Cys | 50 |
| ATG | GAA | GAA | AAG | TGT | AGT | TTT | GAA | GAA | GCA | CGA | GAA | GTT | TTT | GAA | AAC | 198 |
| Met | Glu | Glu | Lys | Cys | Ser | Phe | Glu | Glu | Ala | Arg | Glu | Val | Phe | Glu | Asn | 66 |
| ACT | GAA | AGA | ACA | ACT | GAA | TTT | TGG | AAG | CAG | TAT | GTT | GAT | GGA | GAT | CAG | 246 |
| Thr | Glu | Arg | Thr | Thr | Glu | Phe | Trp | Lys | Gln | Tyr | Val | Asp | Gly | Asp | Gln | 82 |
| TGT | GAG | TCC | AAT | CCA | TGT | TTA | AAT | GGC | GGC | AGT | TGC | AAG | GAT | GAC | ATT | |
| Cys | Glu | Ser | Asn | Pro | Cys | Leu | Asn | Gly | Gly | Ser | Cys | Lys | Asp | Asp | Ile | |
| AAT | TCC | TAT | GAA | TGT | TGG | TGT | CCC | TTT | GGA | TTT | GAA | GGA | AAG | AAC | TGT | |
| Asn | Ser | Tyr | Glu | Cys | Trp | Cys | Pro | Phe | Gly | Phe | Glu | Gly | Lys | Asn | Cys | |

FIG. 4A

```
GAA TTA GAT GTA ACA TGT AAC ATT AAG AAT GGC AGA TGC GAG CAG TTT    294
Glu Leu Asp Val Thr Cys Asn Ile Lys Asn Gly Arg Cys Glu Gln Phe     98
        |85 FIX-EGF2 ->

TGT AAA AAT AGT GCT GAT AAC AAG GTG GTT TGC TCC TGT ACT GAG GAA    342
Cys Lys Asn Ser Ala Asp Asn Lys Val Val Cys Ser Cys Thr Glu Gly    114

TAT CGA CTT GCA GAA AAC CAG AAG TCC TGT GAA CCA GCA GTG CCA TTT    390
Tyr Arg Leu Ala Glu Asn Gln Lys Ser Cys Glu Pro Ala Val Pro Phe    130

CCA TGT GGA AGA GTT TCT GTT TCA CAA ACT TCT AAG CTC ACC CGT GCT    438
Pro Cys Gly Arg Val Ser Val Ser Gln Thr Ser Lys Leu Thr Arg Ala    146

GAG ACT GTT TTT CCT GAT GTG GAC TAT GTA AAT TCT ACT GAA GCT GAA    486
Glu Thr Val Phe Pro Asp Val Asp Tyr Val Asn Ser Thr Glu Ala Glu    162

ACC ATT TTG GAT AAC ATC ACT CAA AGC ACC CAA TCA TTT AAT GAC TTC    534
Thr Ile Leu Asp Asn Ile Thr Gln Ser Thr Gln Ser Phe Asn Asp Phe    178

ACT CGG GTT GTT GGT GGA GAA GAT GCC AAA CCA GGT CAA TTC CCT TGG    582
Thr Arg Val Val Gly Gly Glu Asp Ala Lys Pro Gly Gln Phe Pro Trp    194
        |181 FIX-CD ->

CAG GTT GTT TTG AAT GGT AAA GTT GAT GCA TTC TGT GGA GGC TCT ATC    630
Gln Val Val Leu Asn Gly Lys Val Asp Ala Phe Cys Gly Gly Ser Ile    210
```

FIG. 4B

```
GTT AAT GAA AAA TGG ATT GTA ACT GCT GCC CAC TGT GTT GAA ACT GGT    678
Val Asn Glu Lys Trp Ile Val Thr Ala Ala His Cys Val Glu Thr Gly    226

GTT AAA ATT ACA GTT GTC GCA GGT GAA CAT AAT ATT GAG GAG ACA GAA    726
Val Lys Ile Thr Val Val Ala Gly Glu His Asn Ile Glu Glu Thr Glu    242

CAT ACA GAG CAA AAG CGA AAT GTG ATT CGA ATT ATT CCT CAC CAC AAC    774
His Thr Glu Gln Lys Arg Asn Val Ile Arg Ile Ile Pro His His Asn    258

TAG AAT GCA GCT ATT AAT AAG TAC AAC CAT GAG ATT GCG CTT CTG GAA    822
Tyr Asn Ala Ala Ile Asn Lys Tyr Asn His Asp Ile Ala Leu Leu Glu    274

CTG GAC GAA CCC TTA GTG CTA AAC AGC TAC GTT ACA CCT ATT TGG ATT    870
Leu Asp Glu Pro Leu Val Leu Asn Ser Tyr Val Thr Pro Ile Cys Ile    290
             278|

GCT GAC AAG GAA TAC ACG AAC ATC TTC CTC AAA TTT GGA TCT GGC TAT    918
Ala Asp Lys Glu Tyr Thr Asn Ile Phe Leu Lys Phe Gly Ser Gly Tyr    306

GTA AGT GGC TGG GGA AGA GTC TTC CAC AAA GGG AGA TCA GCT TTA GTT    966
Val Ser Gly Trp Gly Arg Val Phe His Lyn Gly Arg Ser Ala Leu Val    322

CTT CAG TAC CTT AGA GTT CCA CTT GAC CGA ACA TGT CTT CGA            1014
Leu Gln Tyr Leu Arg Val Pro Leu Val Asp Arg Ala Thr Cys Leu Arg    338
```

FIG. 4C

```
TCT ACA AAG TTC ACC ATC TAT AAC AAC ATG TTC TGT GCT GGC TTC CAT    1062
Ser Thr Lys Phe Thr Ile Tyr Asn Asn Met Phe Cys Ala Gly Phe His     354

GAA GGA AGA GAT TAA AGT CAA GGA GAT AGT GGG GGA CCC AAT GTT        1110
Glu Gly Arg Asp Ser Cys Gln Gly Asp Ser Gly Gly Pro His Val         370

ACT GAA GTG GAA GGG ACC AGT TTC TTA ACT GGA ATT ATT AGC TGG GGT    1158
Thr Glu Val Glu Gly Thr Ser Phe Leu Thr Gly Ile Ile Ser Trp Gly     386

GAA GAG TGT GCA ATG AAA GGC AAA TAT GGA ATA TAT ACC AAG GTA TCC    1206
Glu Glu Cys Ala Met Lys Gly Lys Tyr Gly Ile Tyr Thr Lys Val Ser     402

CGG TAT GTC AAC TGG ATT AAG GAA AAA ACA AAG CTC ACT TAA TGA        1251
Arg Tyr Val Asn Trp Ile Lys Glu Lys Thr Lys Leu Thr End End         415
                                                <- 1245|
```

FIG. 4D

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (ii) MOLECULE TYPE: other nucleic acid
      (A) DESCRIPTION:   /desc = "primer"

(xi) SEQUENCE DESCRIPTION: SEQ ID NO: 1:

AAAAAAGAAT TCTCATGATC GTGGGAGGCC AGGAATGCAA G              41

(2) INFORMATION FOR SEQ ID NO: 2:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (ii) MOLECULE TYPE: other nucleic acid
      (A) DESCRIPTION:   /desc = "primer"

(xi) SEQUENCE DESCRIPTION: SEQ ID NO: 2:

AAAAAAAAGC TTCATTACTT GGCCTTGGGC AAGCCCCTGG T              41

(2) INFORMATION FOR SEQ ID NO: 3:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 3:

```
AATTCATTAA AGAGGAGAAA TTAAAATGCA TCACCACCAC GACGATGACG ACAAGATCGT     60

GGGAGGCCAG GAATGCA                                                   77
```

(2) INFORMATION FOR SEQ ID NO: 4:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 4:

```
CATTCCTGGC CTCCCACGAT CTTGTCGTCA TCGTCGTGGT GGTGATGCAT TTTAATTTCT     60

CCTCTTTAAT G                                                         71
```

(2) INFORMATION FOR SEQ ID NO: 5:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 5:

```
AAAAAAGAAT TCATTAAAGA GGAGAAATTA AAATGCGGAA GCTCTGCAGC CTGGACAAC      59
```

(2) INFORMATION FOR SEQ ID NO: 6:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 6:

```
AAAAAAGAAT TCATTAAAGA GGAGAAATTA AAATGTGCGG TAAACAGACC CTGGAACG       58
```

(2) INFORMATION FOR SEQ ID NO: 7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (A) DESCRIPTION:   /desc = "primer"

(xi) SEQUENCE DESCRIPTION: SEQ ID NO: 7:

AAAAAACCAT GGTTGCTCAG GCTACCAGCA GCAGC                              35

(2) INFORMATION FOR SEQ ID NO: 8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 8:

AAAAAACCAT GGTTGTTGGT GGAGAAGATG CCAAACC                            37

(2) INFORMATION FOR SEQ ID NO: 9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 9:

AAAAAAAAGC TTCATTAAGT GAGCTTTGTT TTTTCCTTAA TC                      42

(2) INFORMATION FOR SEQ ID NO: 10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 10:

AAAAAACCAT GGATGTAACA TGTAACATTA AGAATGGCA                          39

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 11:

GGGTTCGTCC AGTTCCAGAA GGGC                                          24

(2) INFORMATION FOR SEQ ID NO: 12:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: other nucleic acid
            (A) DESCRIPTION:    /desc = "primer"

(xi) SEQUENCE DESCRIPTION: SEQ ID NO: 12:

AAAAAAAGGC CTGCATTCCC ACAGGGCCCT ACCCCTGTGG AAGAGTTTCT GTTTCACAAA      60

C                                                                     61

(2) INFORMATION FOR SEQ ID NO: 13:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "primer"

(xi) SEQUENCE DESCRIPTION: SEQ ID NO: 13:

AAAAAATCCG GAAGGCAAAT AGGTGTAACG TAGCTGTTTA GC                         42

(2) INFORMATION FOR SEQ ID NO: 14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "primer"

(xi) SEQUENCE DESCRIPTION: SEQ ID NO: 14:

AAAAAATCCG GAGCGTGACT GGGCCGAGTC C                                     31

(2) INFORMATION FOR SEQ ID NO: 15:

(i) SEQUENCE CHARACTERISTICS:
        (A) LENGTH: 1404 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

CTGCTCGGGG AAAGTCTGTT CATCCGCAGG GAGCAGGCCA ACAACATCCT GGCGAGGGTC      60

ACGAGGGCCA ATTCCTTTCT TGAAGAGATG AAGAAAGGAC ACCTCGAAAG AGAGTGCATG     120

GAAGAGACCT GCTCATACGA AGAGGCCCGC GAGGTCTTTG AGGACAGCGA CAAGACGAAT     180

GAATTCTGGA ATAAATACAA AGATGGCGAC CAGTGTGAGA CCAGTCCTTG CCAGAACCAG     240

GGCAAATGTA AAGACGGCCT CGGGGAATAC ACCTGCACCT GTTTAGAAGG ATTCGAAGGC     300

AAAAACTGTG AATTATTCAC ACGGAAGCTC TGCAGCCTGG ACAACGGGGA CTGTGACCAG     360

TTCTGCCACG AGGAACAGAA CTCTGTGGTG TGCTCCTGCG CCCGCGGGTA CACCCTGGCT     420

GACAACGGCA AGGCCTGCAT TCCCACAGGG CCCTACCCCT GTGGGAAACA GACCCTGGAA     480

CGCAGGAAGA GGTCAGTGGC CCAGGCCACC AGCAGCAGCG GGGAGGCCCC TGACAGCATC     540

ACATGGAAGC CATATGATGC AGCCGACCTG GACCCCACCG AGAACCCCTT CGACCTGCTT     600

GACTTCAACC AGACGCAGCC TGAGAGGGGC GACAACAACC TCACCAGGAT CGTGGGAGGC     660

CAGGAATGCA AGGACGGGGA GTGTCCCTGG CAGGCCCTGC TCATCAATGA GGAAAACGAG     720

GGTTTCTGTG GTGGAACCAT TCTGAGCGAG TTCTACATCC TAACGGCAGC CCACTGTCTC     780

```
TACCAAGCCA AGAGATTCGA AGGGGACCGG AACACGGAGC AGGAGGAGGG CGGTGAGGCG      840

GTGCACGAGG TGGAGGTGGT CATCAAGCAC AACCGGTTCA CAAAGGAGAC CTATGACTTC      900

GACATCGCCG TGCTCCGGCT CAAGACCCCC ATCACCTTCC GCATGAACGT GGCGCCTGCC      960

TGCCTCCCCG AGCGTGACTG GGCCGAGTCC ACGCTGATGA CGCAGAAGAC GGGGATTGTG     1020

AGCGGCTTCG GGCGCACCCA CGAGAAGGGC CGGCAGTCCA CCAGGCTCAA GATGCTGGAG     1080

GTGCCCTACG TGGACCGCAA CAGCTGCAAG CTGTCCAGCA GCTTCATCAT CACCCAGAAC     1140

ATGTTCTGTG CCGGCTACGA CACCAAGCAG GAGGATGCCT GCCAGGGGGA CAGCGGGGGC     1200

CCGCACGTCA CCCGCTTCAA GGACACCTAC TTCGTGACAG GCATCGTCAG CTGGGGAGAG     1260

GGCTGTGCCC GTAAGGGGAA GTACGGGATC TACACCAAGG TCACCGCCTT CCTCAAGTGG     1320

ATCGACAGGT CCATGAAAAC CAGGGGCTTG CCCAAGGCCA AGAGCCATGC CCCGGAGGTC     1380

ATAACGTCCT CTCCATTAAA GTGA                                           1404

(2) INFORMATION FOR SEQ ID NO: 16:

(i) SEQUENCE CHARACTERISTICS:
         (A) LENGTH: 1389 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 16:

ATGCAGCGCG TGAACATGAT CATGGCAGAA TCACCAGGCC TCATCACCAT CTGCCTTTTA       60

GGATATCTAC TCAGTGCTGA ATGTACAGTT TTTCTTGATC ATGAAAACGC CAACAAAATT      120

CTGAATCGGC CAAAGAGGTA TAATTCAGGT AAATTGGAAG AGTTTGTTCA AGGGAACCTT      180

GAGAGAGAAT GTATGGAAGA AAAGTGTAGT TTTGAAGAAG CACGAGAAGT TTTTGAAAAC      240

ACTGAAAGAA CAACTGAATT TTGGAAGCAG TATGTTGATG GAGATCAGTG TGAGTCCAAT      300

CCATGTTTAA ATGGCGGCAG TTGCAAGGAT GACATTAATT CCTATGAATG TTGGTGTCCC      360

TTTGGATTTG AAGGAAAGAA CTGTGAATTA GATGTAACAT GTAACATTAA GAATGGCAGA      420

TGCGAGCAGT TTTGTAAAAA TAGTGCTGAT AACAAGGTGG TTTGCTCCTG TACTGAGGGA      480

TATCGACTTG CAGAAAACCA GAAGTCCTGT GAACCAGCAG TGCCATTTCC ATGTGGAAGA      540

GTTTCTGTTT CACAAACTTC TAAGCTCACC CGTGCTGAGA CTGTTTTTCC TGATGTGGAC      600

TATGTAAATT CTACTGAAGC TGAAACCATT TTGGATAACA TCACTCAAAG CACCCAATCA      660

TTTAATGACT TCACTCGGGT TGTTGGTGGA GAAGATGCCA AACCAGGTCA ATTCCCTTGG      720

CAGGTTGTTT TGAATGGTAA AGTTGATGCA TTCTGTGGAG GCTCTATCGT TAATGAAAAA      780

TGGATTGTAA CTGCTGCCCA CTGTGTTGAA ACTGGTGTTA AAATTACAGT TGTCGCAGGT      840

GAACATAATA TTGAGGAGAC AGAACATACA GAGCAAAAGC GAAATGTGAT TCGAATTATT      900

CCTCACCACA ACTACAATGC AGCTATTAAT AAGTACAACC ATGACATTGC CCTTCTGGAA      960

CTGGACGAAC CCTTAGTGCT AAACAGCTAC GTTACACCTA TTTGCATTGC TGACAAGGAA     1020

TACACGAACA TCTTCCTCAA ATTTGGATCT GGCTATGTAA GTGGCTGGGG AAGAGTCTTC     1080

CACAAAGGGA GATCAGCTTT AGTTCTTCAG TACCTTAGAG TTCCACTTGT TGACCGAGCC     1140

ACATGTCTTC GATCTACAAA GTTCACCATC TATAACAACA TGTTCTGTGC TGGCTTCCAT     1200

GAAGGAGGTA GAGATTCATG TCAAGGAGAT AGTGGGGGAC CCATGTTAC TGAAGTGGAA      1260

GGGACCAGTT TCTTAACTGG AATTATTAGC TGGGGTGAAG AGTGTGCAAT GAAAGGCAAA     1320
```

```
TATGGAATAT ATACCAAGGT ATCCCGGTAT GTCAACTGGA TTAAGGAAAA AACAAAGCTC    1380

ACTTAATGA                                                           1389
```

(2) INFORMATION FOR SEQ ID NO: 17:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

```
Met His His His His Asp Asp Asp Asp Lys
1               5                   10
```

RECOMBINANT BLOOD-COAGULATION PROTEASES

The invention concerns truncated post-translationally non-modif ied blood plasma protease variants of the factor IX gene family (FVII, FIX, FX and protein C) composed of an EFG2 domain, activation peptide (AP) and catalytic domain (CD) as well as the process for their production by expression in a host cell, preferably in a microorganism, renaturation in vitro and subsequent activation with a suitable protease.

The blood plasma protease variants according to the invention are suitable for finding (screening) inhibitors, for the production of co-crystals composed of a protease variant and inhibitor for the purpose of X-ray structure analysis and drug modelling and as diagnostic test: components in activator tests.

Blood plasma proteases play a role in blood coagulation, wound closure by fibrin formation as well as in fibrinolysis i.e. clot dissolution in wound healing. After an injury the injury signal is amplified by the sequential activation (specific proteolysis) of inactive proenzymes to form active enzymes which initiates blood coagulation and ensures a rapid wound closure. Blood coagulation can be initiated by two paths, the intrinsic path in which all protein components are present in the blood and the extrinsic path in which a membrane protein, the so-called tissue factor plays a critical role.

The molecular mechanism of blood homeostasis (blood coagulation, fibrinolysis and the regulation of this equilibrium) and the components that are involved in this are comprehensively described in several review articles (Furie, B. and Furie, B. C., Cell 53 (1988) 505–518; Davie, E. W. et al., Biochem. 30 (1991) 10363–10379; Bergmeyer, H. U. (ed.): Methods of Enzymatic Analysis, Vol. V, chapter 3, 3rd ed., Academic Press, New York (1983)).

The proteases of the blood coagulation cascade are very complex proteins. As a rule they can only be isolated in a complicated manner from the natural raw material source, the blood plasma, in a limited amount, with varying quality, homogeneity and purity (Van Dam-Mieras, M. C. E. et al., In: Bergmeyer, H. U. (ed.), Methods of Enzymatic Analysis, Vol. V, 3rd ed., page 365–394, Academic Press, New York (1983)). They play an important role in the regulation of blood homeostasis which is the equilibrium between blood coagulation, clot formation and dissolution. This well-regulated system can become unbalanced by genetic defects such as haemophilia A (defective factor VIII) and haemophilia B (defective factor IX), as well as by acute disorders such as e.g. in cardiac infarction, embolism and stroke.

There is therefore a need for substances which can influence the system of blood coagulation and fibrinolysis according to the medical requirements. For example recombinantly produced factor VIII or factor IX or recently also factor VII are used to treat haemophilia A and B. tPA (tissue type plasminogen activator) and streptokinase (bacterial protease) are used for example for clot lysis e.g. after cardiac infarction. In addition to complex proteins, substances such as hirudin (peptide composed of 65 amino acids, specific thrombin inhibitor), heparin (heteroglycan, thrombin inhibition/cofactor) and vitamin K antagonists (inhibitors of γ-carboxylation; Glu residues of the Gla domain) are also used to inhibit blood coagulation. However, the available substances are often still very expensive (protein factors) and not ideal with regard to their medical application (side effects) so that there is a need for medicaments which can be used to specifically modulate blood coagulation and clot lysis.

The search for new modulators (activators, inhibitors) of blood coagulation, fibrinolysis and homeostasis can for example be carried out by screening substance libraries and subsequently improving an identified lead structure by drug modelling. For this it is necessary that the key protein(s) [target(s)] are available in an adequate amount and quality for screening and for crystallization investigations (e.g. improvement of the lead structure by the specific prediction of changes based on the 3D structure of the protein component and lead structure).

The activated serine proteases thrombin, FVIIa, FIXa, FXa, FXIa, FXIIa, kallikrein (blood coagulation), tPA, urokinase, plasmin (fibrinolysis) and activated protein C (regulatory anticoagulant) and inactive precursors (zymogens) thereof are for example attractive targets within homeostasis.

The isolation of inactive serine proteases (zymogens) from blood plasma and the subsequent activation by proteolysis is difficult, time-consuming, expensive and often does not yield the amount and quality that is for example desired for crystallization experiments. For example the plasma concentration of the inactive protease zymogens FX, FIX and FVII is only 10, 5 and 0.5 mg/l respectively (Furie, B. and Furie B. C., Cell 53 (1988) 505–518). Moreover the protease preparations isolated from the plasma and activated in vitro are often very heterogeneous and unstable. Furthermore non-uniform post-translational modifications (e.g. carbohydrate groups) impede the crystallization experiments.

Blood plasma proteases are complex glycoproteins that belong to the serine protease family. They are synthesized in the liver as inactive proenzymes (zymogens), secreted into the blood and are activated when required by specific proteolysis i.e. by cleavage of one or two peptide bonds. They are structurally very similar with regard to the arrangement of their protein domains and their composition (Furie, B. and Furie, B. C., Cell 53 (1988) 505–518).

According to Furie B. and Furie, B. C. the proteases of the factor IX family (factor VII, IX, X and protein C) are composed of a propeptide, a GLA domain, an aromatic amino acid stack domain, two EGF domains (EGF1 and EGF2), a zymogen activation domain (activation peptide, AP) and a catalytic protease domain (CD).

Furthermore the blood plasma proteases are post-translationally modified during secretion:

11–12 disulfide bridges

N- and/or O-glycosylation (GLA domain and activation peptide)

Bharadwaj, D. et al., J. Biol. Chem. 270 (1995) 6537–6542

Medved, L. V. et al., J. Biol. Chem. 270 (1995) 13652–13659 cleavage of the propeptide

γ-carboxylation of Glu residues (GLA domain)

β-hydroxylation of an Asp residue (EGF domains)

cleavage of the zymogen region (partially)

After activation of the zymogens (zymogenic form of the protein) by specific cleavage of one or two peptide bonds (activation peptide), the enzymatically active proteases are composed of two chains which, in accordance with their molecular weight, are referred to as the heavy and light chain. In the factor IX protease family the two chains are held together by an intermolecular disulfide bridge between the EGF2 domain and the protease domain. The zymogen-enzyme transformation (activation) leads to conformation changes within the protease domain. This enables an essential salt bridge necessary for the protease activity to form between the N-terminal amino acid of the prc)tease domain and an Asp residue within the protease domain. The N-terminal region is very critical for this subgroup of serine proteases and should not be modified. Only then is it possible for the typical active site of the serine proteases to form with the catalytic triad composed of Ser, Asp and His (Blow, D. M.: Acc. Chem. Res. 9 (1976) 145–152; Polgar, L.: In: Mechanisms of protease action. Boca Raton, Fla., CRC Press, chapter 3 (1989).

Blood plasma proteases can be produced in a classical manner by isolating the inactive zymogens from the blood and subsequently activating them or they can be produced recombinantly by expressing the corresponding cDNA in a suitable mammalian cell line or in yeast.

Production of Blood Plasma Proteases by Expression/secretion of the Zymogens or Active Proteases by Means of Eukaryotic Host/vector Systems FVII: Hagen, F. S. et al., EPS 0200421; Pedersen, A. H. et al., Biochem. 28 (1989) 9391–9336; FIX: Lin, S.-W. et al., J. Biol. Chem. 265 (1990) 144–150; FX: Wolf, D. L. et al., J. Biol. Chem. 266 (1991) 13726–13730; Protein C: Bang, N. U. et al., EPS 0191606.

As a rule host cells are used which are able to post-translationally modify the blood plasma proteases like the native enzyme during the secretion process. The zymogen-enzyme transformation is then carried out subsequently during the downstream processing e.g. by using an activator from snake venom in the case of prothrombin or factor X (Sheehan, J. P. et al., J. Biol. Chem. 268 (1993) 3639–3645; Fujikawa, K. et al. Biochem. 11 (1972) 4892–4898).

For the purpose of zymogen-enzyme activation in vivo (already during secretion), the natural zymogen cleavage sites or the entire activation peptide were substituted by protease cleavage sites (several adjacent basic amino acids) which can be cleaved by specifically cleaving proteases that occur naturally in the secretion path of the host cell such as e.g. Kex2 (yeast) or PACE (mammalian cell lines). (FX: Wolf, D. L. et al., J. Biol. Chem. 266 (1991) 13726–13730; Prothrombin: Holly, R. D. and Foster, D. C., WO 93/13208).

The production or protease variants (FX: Rezaie, A. R: et al., J. Biol. Chem. 268 (1993) 8176–8180); FIX: Zhong, D. G. et al., Proc. Natl. Acad. Sci. USA 91 (1994) 3574–3578), mutants (FX: Rezaie, A. R. et al., J. Biol. Chem. 269 (1994) 21495–21499; Thrombin: Yee, J. et al., J. Biol. Chem. 269 (1994) 17965–17970); FVII: Nicolaisen, E. M. et al., WO 88/10295) and chimeras e.g. composed as FIX and FX (Lin, S.-W. et al., J. Biol. Chem. 265 (1990) 144–150; Hertzberg, M. S. et al., J Biol. Chem. 267 (1992) 14759–14766) by means of eukaryotic host/vector systems is also known.

Disadvantages of Expression in Eukaryotic Mammalian Cell Lines:
- time-consuming
- limited with regard to expression output
- expensive
- post-translational modifications

Production of Blood Plasma Proteases by Expression in Prokaryotes and Subsequent Renaturation of the Expression Product Thogersen, H. C. et al. (WO 94/18227) describe the renaturation of FX variants my means of a cyclic renaturation process in which the inactive FX protein is immobilized in a chromatographic column by means of a metal chelate complex (poly(His)-affinity handle).

A fusion protein is used for this composed of a truncated FX variant (EGF1, EGF2 and protease domain), an additional FXa protease recognition sequence and an attachment aid at the C-terminus of the catalytic domain composed of 6 histidine residues.

Disadvantages:
- A fusion protein composed of protease and poly-his attachment aid must be constructed.
- The renaturation process is very complicated.
  - many renaturation cycles are necessary
  - complex apparatus
  - the yield is only 10%
- The attachment aid may have to be removed after the renaturation.
- The autocatalysis only removes the poly-His tail but not the additionally introduced FXa cleavage site.

DiBella, E. E. et al. (J. Biol. Chem. 270 (1995) 163–169) describe the renaturation of a truncated thrombin variant (prethrombin-2) composed of an A chain (49 amino acids) and a B chain (295 amino acids).

However, an analogous factor Xa variant composed of the activation peptide and protease domain (see example 4) cannot be renatured. The EFG2 domain is necessary in addition to the zymogen region (activation peptide composed of ca. 50 amino acids) for FXa renaturation. This also applies to all members of the FIX protein family (FVII, FIX, FX and protein C).

Thrombin is not a member of the FIX gene family and has two kringle domains instead of two EGF domains.

It was surprisingly found that enzymatically active proteins with serine protease activity can be produced by expression of a corresponding DNA in prokaryotes, renaturation of the expression product and enzymatic cleavage if they are composed of a serine protease domain (catalytic domain), N-terminally linked to a zymogen activation domain and an EGF domain (EGF1 and/or EGF2).

The specificity of the active and truncated serine proteases according to the invention of the factor IX family are unchanged (identical) and consequently they can be used in activity tests as well as to screen for new modulators (activators, inhibitors).

It was not possible to produce an enzymatically active protease domain by expression of a DNA coding only for the catalytic domain and renaturation of the inactive expression product.

The desired enzymatically active protease domains of e.g. FIXa and FXa could also not be produced by N-terminal protease domain fusion proteins with a selective protease cleavage site (e.g. enterokinase cleavage site). It was not possible to renature the expression products according to the prior art.

The invention concerns a non-glycosylated, enzymatically active protein with serine protease activity and its zyomogenic precursor form composed of the following domains of a protease from the factor IX family:
a) the catalytic domain, N-terminally linked with
b) a zymogen activation domain (activation peptide), N-terminally linked with
c) an EGF1 and/or EGF2 domain preferably EGF2 or EGF1 and EGF2).

The zymogen activation domain is preferably composed of an oligopeptide with up to 50 amino acids. After cleavage of the inventive zymogenic (inactive) one chain form in the zymogen activation domain, a two chain active protease is formed. In the two chain form the two chains are linked by an intermolecular disulfide bridge (interchain) (FIG. 1 and FIG. 2).

The proteins according to the invention are preferably composed of the EGF2 domain, the zymogen activation domain and the catalytic domain of factor X and/or factor IX. A protein is also preferred which is composed of the EGF2 domain and the catalytic domain of factor X as well as the activation peptide of factor IX. A protein is particularly preferred which is composed of the N-terminal part of the factor X EGF2 domain (amino acid position 108–154, FIG. 3), the C-terminal part of the factor IX EGF2-domain, the factor IX activation peptide and the factor IX N-terminal half-side (amino acid position 133–289, FIG. 4) and the factor X C-terminal half-side (amino acid position 322–454, FIG. 3).

The zymogens and active proteases of the factor IX family according to the invention can be used instead of the natural zymogens and proteases. Advantageous applications are for example the use as a restriction protease (preferably factor Xa) in biotechnology, as a component of an enzymatic method of determination in diagnostics especially for the indirect determination of blood coagulation protease activities (preferably factor IXa determination). A further application is as a target in screening assays to search for modulators (activators, inhibitors) of blood coagulation, fibrinolysis or homeostasis. Finally the proteins according to the invention provide serine proteases that can be crystallized which can be advantageously used for crystallization investigations (preferably co-crystallization with activators and inhibitors).

The active proteases of the factor IX family (factor IXa, factor Xa, factor VIIa and protein C) according to the invention are particularly preferably used to identify inhibitors. In this case the direct determination of factor IXa and the identification of factor IXa inhibitors is especially preferred. Furthermore the zymogens according to the invention can be used as ingredients in a diagnostic test. In this case the zymogen according to the invention (e.g. factor X) is activated by the protease to be determined (e.g. factor IXa). The activated zymogen (e.g. factor Xa) then cleaves a chromogenic peptide Substrate (e.g. Chromozym X) and generates a measurement signal (e.g. p-nitroaniline). The colour change that occurs is a measure of the concentration of factor IXa in the sample and is proportional to the protease activity to be determined.

A spacer with up to 50 amino acids is preferably inserted between the zymogen activation domain and the EGF domain (or the EGF domains). When the zymogenic one chain form according to the invention is cleaved in the zymogen activation domain, an active protein is obtained in a two chain form. Both chains are linked by an intermolecular disulfide bridge in the two chain form (FIG. 1 and FIG. 2).

The proteins according to the invention are preferably composed of the EGF2 domain, the activation peptide and the catalytic domain of factor X and/or factor IX. A protein is also preferred which is composed of the EGF2 domain and the catalytic domain of factor X as well as the activation domain of factor IX.

Methods
Recombinant DNA Technique

Standard methods were used to manipulate DNA as described in Sambrook, J. et al. (1989) In: Molecular cloning: A laboratory manual. Cold Spring Harbor Laboratory Press, Cold Spring Harbor, N.Y. The molecular biological reagents were used according to the manufacturer's instructions.

Protein Determination

The protein concentration of the protease variants was determined by determining the optical density (OD) at 280 nm using the molar extinction coefficients calculated on the basis of the amino acid sequence.

Expression Vector

The vector for the expression of the blood coagulation protease variants is based on the expression vector pSAM-CORE for core-streptavidin. The preparation and description of the plasmid p-SAM-CORE is described. by Kopetzki, E. et al., in WO 93/09144.

The core-streptavidin gene was replaced by the desired protease variant gene in the pSSM-CORE vector.

The following examples, publications, the sequence protocol and the figures further elucidate the invention, the protective scope of which results from the patent claims. The described methods are to be understood as examples which also still describe the subject matter of the invention even after modifications.

DESCRIPTION OF THE FIGURES

FIG. 3 shows the nucleotide and amino acid sequence for FX given in Kaul, R. K. et al. (Gene 41 (1986) 311–314) (the nucleotide sequence is shown in SEQ ID NO:15).

FIG. 4 shows the nucleotide and amino acid sequence for FIX given in McGraw, R. A. et al. (Proc. Natl. Acad. Sci. USA 82 (1985) 2847–2851) (the nucleotide sequence is shown in SEQ ID NO:16).

EXAMPLE 1

Figure 1:
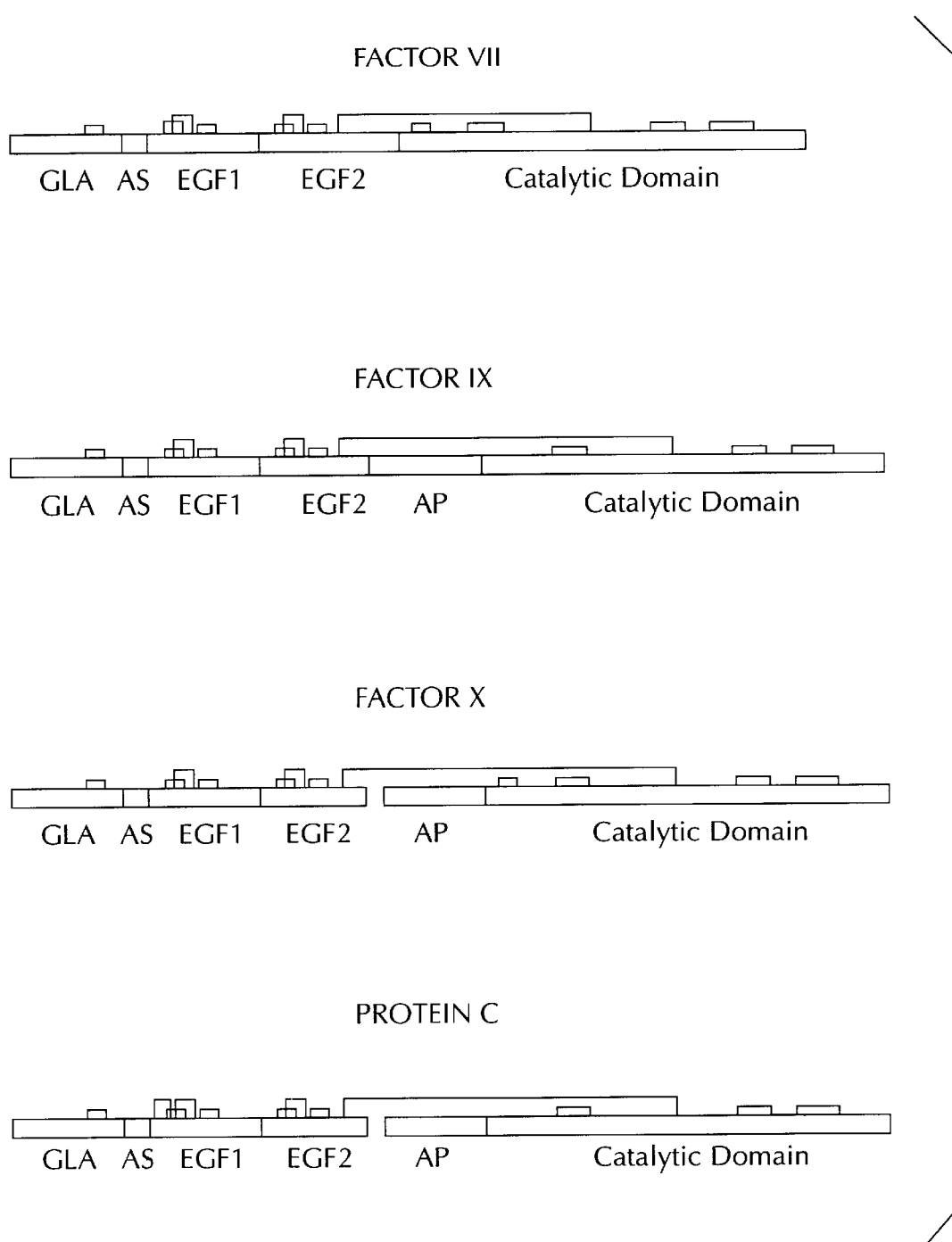
FIG. 1 is a diagram of the blood plasma proteases of the FIX protease family.
Figure 2:
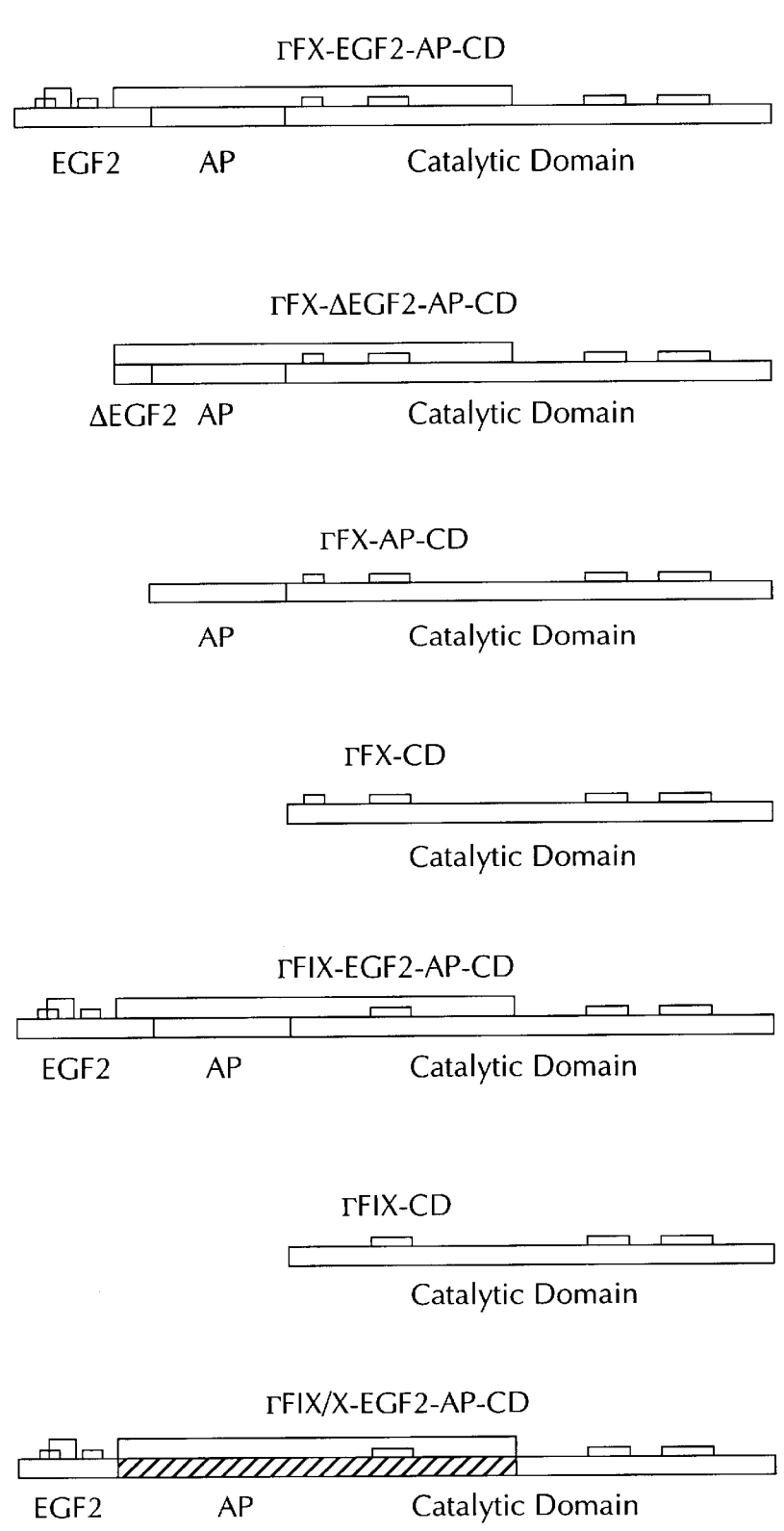
FIG. 2 is a diagram of the constructed truncated FIX, FX and FIX/X chimeric blood plasma proteases. (In the case of rFIX/X-EGF2-AP-CD the factor X part is white and the factor IX part is black) Abbreviations: AP=activation peptide; AA=aromatic amino acid stack domain; CD=catalytic domain; EGF1=epidermal growth factor-like domain 1; EGF2=epidermal growth factor-like domain 2; GLA=γ-carboxyglutamic acid-rich domain.

Cloning the Catalytic Domain of the FX Protease Gene (Plasmid: pFX-CD)

The FX cDNA from bp position 649 to 1362, coding for the FX protease domain from amino acid position 217 to 454 (cDNA sequence acid sequence and amino acid sequence numbering according to the publication of Kaul, R. K. et al., (Gene 41 (1986) 311–314; FIG. 3) was amplified in a polymerase chain reaction (PCR) according to the method of Mullis, K. B. and Faloona, F. A., (Methods Enzymol. 155, (1987) 350–355) using the PCR primers N1 (SEQ ID NO:1) and N2 (SEQ ID NO:2).

```
                EcoRI BspHI
N1: 5'-AAAAAAGAATTCTCATGATCGTGGGAGGCCAGGAATGCAAG-3'
                    MetIleValGlyGlyGlnGluCysLys
              HindIII
N2: 5'-AAAAAAAAGCTTCATTACTTGGCCTTGGGCAAGCCCCTGGT-3'
``` and a commercially available human liver cDNA gene bank (vector: Lambda ZAP® II) from the Stratagene Company (La Jolla, Calif., U.S.A.) as template DNA. The PCR primers introduced a singular BspHI cleavage site and an ATG start codon at the 5' end of the coding region and a singular HindIII cleavage site at the 3' end of the coding region.

The ca. 740 bp long PCR product was digested with the restriction endonucleases BspHI and HindIII and the ca. 725 bp long BspHI/HindIII-FX fragment was ligated into the ca. 2.55 kbp long NcoI/HindIII-pSAM-CORE vector fragment after purification by agarose gel electrophoresis. The desired plasmid pFX-CD was identified by restriction mapping and the FX cDNA sequence isolated by PCR was checked by DNA sequencing.

cleavage site that is upstream in the promoter were used to construct this FX-EK-CD variant gene.

For this the plasmid pFX-CD was digested with the restriction endonucleases EcoRI and BsmI and the ca. 3.25 kbp long EcoRI/BsmI-pFX-CD vector fragment was ligated with the FX-EK-CD DNA adaptor after isolation by means of agarose gel electrophoresis. The FX-EK-CD adaptor was constructed by hybridization from the complementary oligonucleotides N3 (SEQ ID NO:3) and N4 (SEQ ID NO:4) (reaction buffer: 12.5 mmol/l Tris-HCl, pH 7.0 and 12.5 mmol/l $MgCl_2$; N concentration: 1 pmol/60 µl each time).

FX-EK-CD Adaptor

```
N3: 5'-AATTCATTAAAGAGGAGAAATTAAAATGCATCACCACCACGACGATGACGACAAGATCGTGGGAGGCCAGGAATGCA-3'
N4: 5'-CATTCCTGGCCTCCCACGATCTTGTCGTCATCGTCGTGGTGGTGATGCATTTTAATTTCTCCTCTTTAATG-3'
    EcoRI                                                                                    BsmI
N3: 5'-AATTCATTAAAGAGGAGAAATTAAAATGCATCACCACCACGACGATGACGACAAGATCGTGGGAGGCCAGGAATGCA-3
N4: 3'-    GTAATTTCTCCTCTTTAATTTTACGTAGTGGTGGTGCTGCTACTGCTGTTCTAGCACCCTCCGGTCCTTAC -5'
                          MetHisHisHisHisAspAspAspAspLysIleValGlyGlyGlnGluCys
```

EXAMPLE 2

Construction of the FX Protease Gene with an N-terminal (His)$_4$ Tail, Enterokinase Cleavage Site and Catalytic Domain (plasmid: pFX-EK-CD)

The reading frame of the cloned FX-CD gene (see example 1) was linked at the 5' end with a nucleotide sequence which codes for the amino acid sequence MHHHHDDDDK (SEQ ID NO:17) and contains the ATG start codon, a poly-His sequence and an enterokinase cleavage site. The singular BsmI cleavage site located at the 5' end of the FX-CD gene and the neighbouring singular EcoRI

EXAMPLE 3

Cloning of the FX Protease Gene with an EGF2 Domain, Activation Peptide and Catalytic Domain (plasmid: pFX-EGF2-AP-CD)

The FX cDNA from bp position 322 to 1362, coding for the EGF2 domain, the activation peptide and the catalytic protease domain from amino acid position 108 to 454 (cDNA sequence acid sequence and amino acid sequence numbering according to FIG. 3) was amplified by means of PCR using the PCR primers N5 (SEQ ID NO:5) and N2 (SEQ ID NO:2).

```
                    EcoRI
N5: 5'-AAAAAAGAATTCATTAAAGAGGAGAAATTAAAATGCGGAAGCTCTGCAGCCTGGACAAC-3'
                                          MetArgLysLeuCysSerLeuAspAsn
``` and a commercially available human liver cDNA gene bank (vector: Lambda ZAP® II) from the Stratagene Company (La Jolla, Calif., U.S.A.) as template DNA. The PCR primers introduced an ATG start codon and a singular EcoRI cleavage site at the 5' end of the coding region and a singular HindIII cleavage site at the 3' end of the coding region.

The ca. 1.09 kbp long PCR product was digested with the restriction endonucleases EcoRI and BstEII and the ca. 1.02 kbp long EcoRI/BstEII-FX fragment was ligated into the ca. 2.58 kbp long EcoRI/BstEII-pFX-CD vector fragment (example 1) after purification by agarose gel electrophoresis. The desired plasmid pFX-EGF2-AP-CD was identified by restriction mapping and the FX cDNA sequence isolated by PCR was checked by DNA sequencing.

EXAMPLE 4

Construction of the FX Protease Gene with Truncated EGF2 Domain, Activation Peptide and Catalytic Domain (plasmid: pFX-ΔEGF2-AP-CD)

The FX cDNA from bp position 460 to 1362, coding for a truncated EGF2 domain, the activation peptide and the catalytic protease domain from amino acid position 154 to 454 (cDNA sequence acid sequence and amino acid sequence numbering according to FIG. 3) was amplified by means of PCR using the PCR primers N6 (SEQ ID NO:6) and N2 (SEQ ID NO:2).

```
              EcoRI
N6: 5'-AAAAAAGAATTCATTAAAGAGGAGAAATTAAAATGTGcGGtAAACAGACCCTGGAACG-3'
                                      MetCysGlyLysGlnThrLeuGlu
``` and the plasmid pFX-EGF2-AP-CD (example 3) as template DNA. In the PCR the 5' region of the structural gene (amino acid positions 2 and 3) was adapted to the codons preferably used in *E. coli* without changing the protein sequence by means of the N6 primer (ATG environment with optimized codon usage, indicated by the bases written in small letters in the N6 primer).

The ca. 960 bp long PCR product was digested with the restriction endonucleases EcoRI and HindIII and the ca. 950 bp long EcoRI/HindIII-FX fragment was ligated into the ca. 2.53 kbp long EcoRI/HindIII-pSAM-CORE vector fragment (example 1) after purification by agarose gel electrophoresis. The desired plasmid pFX-ΔEGF2-AP-CD was identified by restriction mapping and the FX DNA sequence amplified by PCR was checked by DNA sequencing.

EXAMPLE 5

Construction of the FX Protease Gene with Activation Peptide and Catalytic Domain (plasmid: pFX-AP-CD)

The FX cDNA from bp position 496 to 1362, coding for the activation peptide and the catalytic protease domain from amino acid position 166 to 454 (cDNA sequence and amino acid sequence numbering according to FIG. 3) was amplified by means of PCR using the PCR primers N7 (SEQ ID NO:7) and N2 (SEQ ID NO:2).

```
                NcoI
N7: 5'-AAAAAACCATGGTtGCtCAGGCtACCAGCAGCAGC-3'
              MetValAlaGlnAlaThrSerSerSer
``` and the plasmid pFX-EGF2-AP-CD (example 3) as template DNA. The 5' region of the structural gene (amino acid positions 2, 3 and 5) were adapted to the cc)dons preferably used in *E. coli* without changing the protein sequence by means of the N7 primer (ATG environment with optimized codon usage, indicated by the bases written in small letters in the N7 primer).

The ca. 890 bp long PCR product was digested with the restriction endonucleases NcoI and HindIII and the ca. 880 bp long NcoI/HindIII-FX fragment was ligated into the ca. 2.55 kbp long NcoI/HindIII-pSAM-CORE vector fragment (example 1) after purification by agarose gel electrophoresis. The desired plasmid pFX-AP-CD was identified by restriction mapping and the FX DNA sequence amplified by PCR was checked by DNA sequencing.

EXAMPLE 6

Cloning of the Catalytic Domain of the FIX Protease Gene (plasmid: pFIX-CD)

The FIX cDNA from bp position 690 to 1403, coding for the FIX protease domain from amino acid position 181 to 415 (cDNA sequence and amino acid sequence numbering according the publication of McGraw, R. A. et al. (Proc. Natl. Acad. Sci. USA 82 (1985) 2847–2851; FIG. 4) was amplified using the PCR primers N8 (SEQ ID NO:8) and N9 (SEQ ID NO:9).

```
                NcoI
N8: 5'-AAAAAACCATGGTTGTTGGTGGAGAAGATGCCAAACC-3'
              MetValValGlyGlyGluAspAlaLys
              HindIII
N9: 5'-AAAAAA
       AAGCTTCATTAAGTGAGCTTTGTTTTTTCCTTAATC-3
``` and a commercially available human liver cDNA gene bank (vector: Lambda ZAP® II) from the Stratagene Company (La Jolla, Calif., U.S.A.) as template DNA. The PCR primers introduced a singular NcoI cleavage site and an ATG start codon at the 5' end of the coding region and a singular HindIII cleavage site at the 3' end of the coding region.

The ca. 730 bp long PCR product was digested with the restriction endonucleases NcoI and HindIII and the ca. 720 bp long NcoI/HindIII-FIX fragment was ligated into the ca. 2.55 kbp long NcoI/HindIII-pSAM-CORE vector fragment (example 1) after purification by agarose gel electrophoresis. The desired plasmid PFIX-CD was identified by restriction mapping and the FIX cDNA sequence isolated by PCR was checked by DNA sequencing.

EXMAPLE 7

Construction of the FIX Protease Gene with EGF2 Domain, Activation Peptide and Catalytic Domain (plasmid: pFIX-EGF2-AP-CD)

The FIX cDNA from bp position 402 to 986, coding for the EGF2 domain, the activation peptide and the N-terminal region of the FIXa protease domain from amino acid position 85 to 278 (cDNA sequence and amino acid sequence numbering according to FIG. 4) was amplified using the PCR primers N10 (SEQ ID NO:10) and N11 (SEQ ID NO:11).

```
                 NcoI
N10: 5'-AAAAAACCATGGATGTAACATGTAACATTAAGAATGGCA-3'
               MetAspValThrCysAsnIleLysAsnGly
N11: 5'-GGGTTCGTCCAGTTCCAGAAGGGC-3'
``` and a commercially available human liver cDNA gene bank (vector: Lambda ZAP® II) from the Stratagene Company (La Jolla, Calif., U.S.A.) as template DNA. The PCR primer N10 introduced an ATG start codon at the 5' end of the coding region and a singular NcoI cleavage site.

The ca. 590 bp long PCR product was digested with the restriction endonucleases NcoI and BsmI and the ca. 360 bp long NcoI/BsmI-FIX-EGF2-AP fragment wats ligated into the ca. 3.2 kbp long NcoI/BsmI-pFIX-CD vector fragment (example 6) after purification by agarose gel electrophoresis. The desired plasmid pFIX-EGF2-AP-CD was identified by restriction mapping and the FIX cDNA sequence amplified by PCR was checked by DNA sequencing.

EXAMPLE 8

Construction of a Chimeric Protease Gene Composed of FIX and FX (plasmid: pFIX/X-EGF2-AP-CD)

The chimeric FIX/FX protease gene was composed of the N-terminal part of the FX EGF2 domain (bp position: 322–462; amino acid position: 108–154, FIG. 3), the C-terminal part of the FIX EGF2, the FIX activation peptide and the FIX N-terminal half-side (bp position: 397–867; amino acid position: 133–289; FIG. 4) and the FX C-terminal half-side (bp position: 964–1362; amino acid position: 322–454; FIG. 3).

For this the DNA coding for the C-terminal part of the FIX EGF2, the FIX activation peptide and the FIX N-terminal half-side from bp position 397 to 867 (amino acid position: 133–289; FIG. 4) was amplified in a first PCR reaction using the PCR primers N12 (SEQ ID NO:12) and N13 (SEQ ID NO:13).

```
            StuI
N12: 5'-AAAAAAAGGCCTGCATTCCCACAGGGCCCTACCCCTGTGGAAGAGTTTCTGTTTCACAAAC-3'
                                            GlyArgValSerValSerGln--
                                            |133 FIX-EGF2 ->
            MroI
N13: 5'-AAAAAAtCCgGAAGGCAAATAGGTGTAACGTAGCTGTTTAGC-3'
``` and the plasmid pFIX-EGF2-AP-CD (example 7) as template DNA. The FX-EGF2 DNA sequence was linked with the FIX-EGF2 DNA sequence by means of the 5' overhanging nucleotide sequence of the PCR primer N12. It is composed of the FX DNA sequence from bp position 430 to 462 (FIG. 3) with a singular StuI cleavage site at the 5' end. The FIX DNA was linked with the FX DNA using the 5' overhanging nucleotide sequence of the N13 primer. It is composed of the FX DNA sequence from bp position: 964–970 (FIG. 3). A singular MroI cleavage site was produced in this sequence by two base pair substitutions (indicated by the bases written in small letters in the N13 primer) without changing the protein sequence. The FX C-terminal half-side from bp position: 964–1362 (amino acid position: 322–454; FIG. 3) was amplified in a second PCR reaction using the PCR primers N14 (SEQ ID NO:14) and N2 (SEQ ID NO:2).

```
                MroI
N14: 5'AAAAAAtCCgGAGCGTGACTGGGCCGAGTCC-3
``` and the plasmid pFX-EGF2-AP-CD (example 3) as template DNA. A singular MroI cleavage site was introduced by means of the N14 primer at the 5' end within the coding FX-CD region by two bp substitutions (indicated by the bases written in small letters in the N14 primer) without changing the amino acid sequence.

The first PCR product was digested with StuI and MroI and the second PCR product was digested with MroI and HindIII. Afterwards the ca. 510 bp long StuI/MroI fragment was ligated with the ca. 400 bp long MroI/HindIII fragment and the ca. 2640 bp long StuI/HindIII-pFX-EGF2-AP-CD vector fragment (example 3) in a three fragment ligation. The desired plasmid pFIX/X-EGF2-AP-CD was identified by restriction mapping and the FIX/X DNA sequence amplified by PCR was checked by DNA sequencing.

EXAMPLE 9 a) Expression of the Protease Gene in E. coli

In order to express the protease gene, the E. coli K12 strain UT5600 (Grodberg, J. and Dunn, J. J. J. Bacteriol. 170 (1988) 1245–1253) was transformed in each case with one of the expression plasmids pFX-CD, pFX-EK-CD, pFX-EGF2-AP-CD, pFX-ΔEGF2-AP-CD, pFX-AP-CD, pFIX-CD, pFIX-EGF2-AP-CD and pFIX/X-EGF2-AP-CD (ampicillin resistance) described in examples 1–8 and with the lacIq repressor plasmid pUBS520 (kanamycin resistance, preparation and description see: Brinkmann, U. et al., Gene 85 (1989) 109–114).

The UT5600/pUBS520/cells transformed with the expression plasmids pFX-CD, pFX-EK-CD, pFX-EGF2-AP-CD, pFX-ΔEGF2-AP-CD, pFX-AP-CD, pFIX-CD, pFIX-EGF2-AP-CD and pFIX/X-EGF2-AP-CD were cultured in a shaking culture in DYT medium (1% (w/v) yeast extract, 1% (w/v) Bacto Tryptone, Difco and 5% NaCl) containing 50–100 mg/l ampicillin and 50 mg/l kanamycin at 37° C. up to an optical density at 550 nm ($OD_{550}$) of 0.6–0.9 and subsequently induced with IPTG (final concentration 1–5 mmol/l). After an induction phase of 4–8 hours (h) at 37° C., the cells were harvested by centrifugation (Sorvall RC-5B centrifuge, GS3 rotor, 6000 rpm, 15 min), washed with 50 mmol/l Tris-HCl buffer pH 7.2 and stored at –20° C. until further processing. The cell yield from a 1 l shaking culture was 4–5 g (wet weight).

b) Expression Analysis

The expression of the UT5600/pUBS520/cells transformed with the plasmids pFX-CD, pFX-EK-CD, pFX-EGF2-AP-CD, pFX-ΔEGF2-AP-CD, pFX-AP-CD, pFIX-CD, pFIX-EGF2-AP-CD and pFIX/X-EGF2-AP-CD was analysed. For this purpose cell pellets from in each case 1 ml centrifuged culture medium were resuspended in 0.25 ml 10 mmol/l Tris-HCl, pH 7.2 and the cells were lysed by ultrasonic treatment (2 pulses of 30 s at 50% intensity) using a Sonifier® Cell Disruptor B15 from the Branson Company (Heusenstamm, Germany). The insoluble cell components were sedimented (Eppendorf 5415 centrifuge, 14000 rpm, 5 min) and ⅕ volumes (vol) 5×SDS sample buffer (1×SDS sample buffer: 50 mmol/l Tris-HCl, pH 6.8, 1% SDS, 1% mercaptoethanol, 10% glycerol, 0.001% bromophenol blue) was added to the supernatant. The insoluble cell debris fraction (pellet) was resuspended in 0.3 ml 1×SDS sample buffer containing 6–8 M urea, the samples were incubated for 5 min at 95° C. and centrifuged again. Afterwards the proteins were separated by SDS polyacrylamide gel electrophoresis (PAGE) (Laemmli, U. K., Nature 227 (1970) 680–685) and stained with Coomassie Brilliant Blue R dye.

The protease variants synthesized in E. coli were homogeneous and were exclusively found in the insoluble cell debris fraction (inclusion bodies, IBs). The expression yield was 10–50% relative to the total E. coli protein.

EXAMPLE 10

Cell Lysis, Solubilization and Renaturation of the Protease Variants a) Cell Lysis and Preparation of Inclusion Bodies (IBs)

The cell pellet from 3 l shaking culture (ca. 15 g wet weight) was resuspended in 75 ml 50 mmol/l Tris-HCl, pH 7.2. The suspension was admixed with 0.25 mg/ml lysozyme and it was incubated for 30 min at 0° C. After addition of 2 mmol/l $MgCl_2$ and 10 μg/ml DNase I (Boehringer Mannhein GmbH, catalogue No. 104159) the cells were disrupted mechanically by means of high pressure dispersion in a French® Press from the SLM Amico Company (Urbana, Ill., USA). Subsequently the DNA was digested for 30 min at room temperature (RT). 37.5 ml 50 mmol/l Tris-HCl pH 7.2, 60 mmol/l EDTA, 1.5 mol/l NaCl, 6% Triton X-100 was added to the preparation, it was incubated for a further 30 min at RT and centrifuged in a Sorvall RC-5B centrifuge (GSA Rotor, 12000 rpm, 15 min). The supernatant was discarded, 100 ml 50 mmol/l Tris-HCl, pH 7.2, 20 mmol/l EDTA was added to the pellet, it was incubated for 30 min while stirring at 4° C. and again sedimented. The last wash step was repeated. The purified IBs (1.5–2.0 g wet weight, 25–30% dry mass, 100–150 mg protease) were stored at −20° C. until further processing.

b) Solubilization and Derivatization of the IBs

The purified IBs were dissolved within 1 to 3 hours at room temperature while stirring at a concentration of 100 mg IB pellet (wet weight)/ml corresponding to 5–10 mg/ml protein in 6 mol/l guanidinium-HCl, 100 mmol/l Tris-HCl, 20 mmol/l EDTA, 150 mmol/l GSSG and 15 mmol/l GSH, pH 8.0. Afterwards the pH was adjusted to pH 5.0 and the insoluble components were separated by centrifugation (Sorvall RC-5B centrifuge, SS34 rotor, 16000 rpm, 10 min). The supernatant was dialysed for 24 hours at 4° C. against 100 vol. 4–6 mol/l guanidinium-HCl pH 5.0.

c) Renaturation

The renaturation of the protease variants solubilized in 6 mol/l guanidinium-HCl and derivatized with GSSG/GSH was carried out at 4° C. by repeated (e.g. 3-fold) addition of 0.5 ml IB solubilisate/derivative in each case to 50 ml 50 mmol/l Tris-HCl, 0.5 mol/l arginine, 20 mmol/l $CaCl_2$, 1 mmol/l EDTA and 0.5 mmol/l cysteine, pH 8.5 at intervals of 24 hours and subsequent incubation for 48 hours at 4° C. After completion of the renaturation reaction the insoluble components were separated by filtration with a filtration apparatus from the Satorius Company (Göttingen, Germany) equipped with a deep bed filter K 250 from the Seitz Company (Bad Kreuznach, Germany).

d) Concentration and Dialysis of the Renaturation Preparations

The clear supernatant containing protease was concentrated 10–15-fold by cross-flow filtration in a Minisette (membrane type: Omega 10K) from the Filtron Company (Karlstein, Germany) and dialysed for 24 hours at 4° C. against 100 vol. 20 mmol/l Tris-HCl and 50 mmol/l NaCl, pH 7.2 to remove guanidinium-HCl and arginine. Precipitated protein was removed by centrifugation (Sorvall RC-5B centrifuge, SS34 rotor, 16000 rpm, 20 min) and the clear supernatant was filtered with a Nalgene® disposable filtration unit (pore diameter: 0.2 μm) from the Nalge Company (Rochester, N.Y., USA).

e) Determination of the Renaturation Efficiency

The protein concentration of the renatured, concentrated and filtered renaturation preparations was determined by measuring the optical density (OD) at 280 nm using the molar extinction coefficients calculated on the basis of the amino acid sequences for rFX-CD, rFX-EK-CD, rFX-EGF2-AP-CD, rFX-ΔEGF2-AP-CD, rFX-AP-CD, rFIX-CD, rFIX-EGF2-AP-CD and rFIX/X-EGF2-AP-CD A sample of the renaturation preparations composed of natively folded protease and falsely disulfide-bridged protease oligomers was separated by non-reducing SDS PAGE (example 13b). The desired soluble monomeric protease zymogens were identified by means of the apparent molecular weight and the band strength. The renaturation efficiency was estimated from the comparison (ratio) of the band intensities of monomeric protease zymogens to the remaining bands (protein smear).

| Protease variant | molar extinction coefficient [$cm^2$ $mol^{-1}$] | molecular weight [kDa] | renaturation efficiency [%] |
|---|---|---|---|
| rFX-CD | 33540 | 27.3 | <0.1 |
| rFX-EK-CD | 33540 | 28.4 | <0.1 |
| rFX-EGF2-AP-CD | 43490 | 39.3 | 5–10 |
| rFX-ΔEGF2-AP-CD | 40570 | 34.3 | <0.1 |
| rFX-AP-CD | 40510 | 32.9 | <0.1 |
| rFIX-CD | 41670 | 26.3 | <0.1 |
| rFIX-EGF2-AP-CD | 44650 | 36.9 | 15–20 |
| rFIX/X-EGF2-AP-CD | 43370 | 37.5 | 10–15 |

Result

It was only possible to renature the protease variants with an EGF2 domain, the activation peptide (AP) and catalytic domain (CD).

EXAMPLE 11

Purification of the Renatured Inactivated Protease Variants

The inactive protease variants from the renaturation preparations can, if required, be further purified with chromatographic methods which are known to a person skilled in the art.

a) Purification of the Protease Variants by Ion Exchange Chromatography on Q-Sepharose-ff The concentrated renaturation preparation that had been dialysed against 20 mmol/l Tris-HCl and 50 mmol/l NaCl, pH 8.0 was applied to a Q-Sepharose ff column (1.5×11 cm, V=20 ml; loading capacity: 10 mg protein/ml gel) from the Pharmacia Biotech Company (Freiburg, Germany) (2 column volumes/hour, 2 CV/h) equilibrated with the same buffer and it was washed with the equilibration buffer until the absorbance of the eluate at 280 nm had reached the blank value of the buffer. The bound material was eluted by a gradient of 50–500 mmol/l NaCl in 20 mmol/l Tris-HCl, pH 8.0 (2 CV/h). The proteases were eluted at an NaCl concentration of 100–150 mmol/l. The fractions containing protease were identified by non-reducing and reducing SDS PAGE and the elution peak was pooled.

b) Final Purification of the Inactive Protease Variants by Ion Exchange Chromatography on Heparin-Sepharose CL-6B After chromatography on a Q-Sepharose ff column, the combined fractions containing protease were directly applied (2 CV/h) to a heparin-Sepharose CL-6B column (1.5×11 cm, V=20 ml, loading capacity: 1 mg protein/mL gel) from the Pharmacia Biotech Company (Freiburg, GFR) that had been equilibrated with 20 mmol/l Tris-HCl and 200 mmol/l NaCl, pH 8.0. Afterwards it was washed with equilibration buffer until the absorbance of the eluate at 280 nm reached the blank value for the buffer. The bound material was eluted by a gradient of 0.2–1.0 mol/l NaCl in 20 mmol/l Tris-HCl, pH 8.0 (2 CV/h). The proteases were eluted at a NaCl concentration of 500–600 mmol/l. The fractions containing protease were identified by non-reducing and reducing SDS PAGE, the elution peak was combined and dialysed against 20 mmol/l Tris-HCl, 50–200 mmol/l NaCl, 5 mmol/l CaCl$_2$, pH 7.8.

EXAMPLE 12

Activation and Purification of the Activated Protease Variants

The renatured purified inactive rFIX and rFX protease variants were activated with purified Russel's viper venom (RVV-X) protease. The RVV-X protease was, as described in the publication by Esmon, C. T. (prothrombin activation, doctoral dissertation, Washington University, St. Louis, Mo. (1973)), purified from the commercially available snake venom lyophilisate from the Sigma Aldrich Chemie GmbH Co. (Deisenhofen, GFR) by gel filtration followed by ion exchange chromatography on Q-Sepharose ff.

a) Activation and Purification of rFIX-EGF2-AP-CD Protease Variant with RVV-X

The protease variant rFIX-EGF2-AP-CD was digested at 25° C. at a concentration of 0.5 to 2.0 mg/ml and a protease/substrate ratio of 1:10 to 1:20 in 20 mmol/l Tris-HCl, 50 mmol/l NaCl, 10 mmol/l CaCl$_2$, pH 7.8. The time course of the enzymatic FIX activation was monitored by determining the activity with a chromogenic substrate (see example 13a) until the digestion was completed (plateau, maximum activation). For this purpose samples (10 to 100 µl) were taken from the reaction preparation at intervals of 3–4 h over a period of up to 24 hours and the generated rFIXa activity was determined. After reaching the activation plateau, the RVV-X digest was purified by negative chromatography on Q-Sepharose-ff.

RVV-X and non-activated rFIX-EGF2-AP-CD protease bind under the given conditions to Q-Sepharose-ff, but rFIXa-EGF2-AP-CD protease does not.

The digestion preparation was applied (2 CV/h) to a Q-Sepharose-ff column (1.0×10 cm, V=8 ml) from the Pharmacia Biotech Company (Freiburg, GFR) which had been equilibrated with 20 mmol/l Tris-HCl, 50 mmol/l NaCl, pH 7.8 and the column was developed with equilibration buffer while fractionating. The fractions containing rFIXa-EGF2-AP-CD protease were identified by non-reducing and reducing SDS PAGE and activity determination.

b) Activation and Purification of the rFX-EGF2-AP-CD Protease Variant with RVV-X The protease variant rFX-EGF2-AP-CD was digested at 25° C. at a concentration of 0.5 to 2.0 mg/ml and a protease/substrate ratio of 1:100 to 1:200 in 20 mmol/l Tris-HCl, 50 mmol/l NaCl, 10 mmol/l CaCl$_2$, pH 7.8. The time course of the enzymatic rFX-EGF2-AP-CD activation was monitored by determining the activity with a chromogenic substrate (see example 13a) until the digestion was completed (plateau, maximum activation). For this purpose samples (10 to 100 µl) were taken from the reaction preparation at intervals of 15–30 min over a period of up to 4 hours and the generated FXa activity was determined. After reaching the activation plateau, the active rFXa-EGF2-AP-CD protease was purified by chromatography on benzamidine-Sepharose-CL-6B.

Only the activated rFXa-EGF2-AP-CD protease variant binds under the given conditions to benzamidine-Sepharose-CL-6B.

The digestion preparation was applied (2 CV/h) to a benzamidine-Sepharose-CL-6B column (1.0×10 cm, V=8 ml; loading capacity: 2–3 mg protein/ml gel) from the Pharmacia Biotech Company (Freiburg, GFR) which had been equilibrated with 20 mmol/l Tris-HCl, 200 mmol/l NaCl, pH 8.0 and washed with the equilibration buffer until the absorbance of the eluate at 280 nm reached the blank value of the buffer. The bound material was eluted with 10 mmol/l benzamidine in 20 mmol/l Tris-HCl, 200 mmol/l NaCl, pH 8.0 (2 CV/h). The fractions containing rFXa-EGF2-AP-CD protease were identified by non-reducing and reducing SDS PAGE and activity determination.

c) Activation with RVV-X and Purification of the Chimeric rFIX/X-EGF2-AP-CD Protease Variant The protease variant rFIX/X-EGF2-AP-CD was digested at 25° C. at a concentration of 0.5 to 2.0 mg/ml and a protease/substrate ratio of 1:10 to 1:20 in 20 mmol/l Tris-HCl, 50 mmol/l NaCl, 10 mmol/l CaCl$_2$, pH 7.8. The time course of the enzymatic rFIX/X-EGF2-AP-CD activation was monitored by determining the activity with a chromogenic substrate (see example 13a) until the digestion was completed (plateau, maximum activation). For this purpose samples (10 to 100 µl) were taken from the reaction preparation at intervals of 3–4 h over a period of up to 24 hours and the generated rFIX/Xa-EGF2-AP-CD activity was determined. After reaching the activation plateau, the RVV-X digest was purified by negative chromatography on Q-Sepharose-ff.

RVV-X and non-activated rFIX/X-EGF2-AP-CD protease bind under the given conditions to Q-Sepharose-ff, but the activated rFIX/Xa-EGF2-AP-CD protease variant does not.

The digestion preparation was applied (3 CV/h) to a Q-Sepharose-ff column (1.0×10 cm, V=8 ml) from the Pharmacia Biotech Company (Freiburg, GFR) which had been equilibrated with 20 mmol/l Tris-HCl, 50 mmol/l NaCl, pH 7.8 and the column was developed with equilibration buffer while fractionating. The fractions containing rFIX/Xa-EGF2-AP-CD protease were identified by non-reducing and reducing SDS PAGE and activity determination.

EXAMPLE 13

Characterization of Purified Protease Variants a) Activity Test

The activity of the renatured activated rFIXa-EGF2-AP-CD, rFXa-EGF2-AP-CD and rFIXa/Xa-EGF2-AP-CD protease variants was determined using the chromogenic substrate Chromozym X (Boehringer Mannheim GmbH, Mannheim, GFR, cat.No. 789763). 10–100 µl sample was made up to 200 µl with 190–100 µl 50 mmol/l Tris-HCl, 150 mmol/l NaCl, 5 mml/l CaCl$_2$, 0.1% polyethylene glycol 8K (PEG 8000), pH 8.0, admixed with 20 µl Chromozym X (0.5–40 mmol) and measured at a wavelength of 405 nm and RT against a reagent blank value in an ELISA reader. The activity and the kinetic constants were determined from the linear initial slope according to the Michaelis Menten equation.

b) SDS PAGE

Oligomer and aggregate formation by intermolecular disulfide bridge formation as well as the homogeneity and purity of the renatured activated and purified protease variants were examined by non-reducing (minus mercaptoethanol) and reducing (plus mercaptoethanol) SDS PAGE (Laemmli, U K, Nature 227 (1970) 680–685).

EXAMPLE 14

FX Activator Test

The recombinantly produced highly pure inactive rFX-EGF2-AP-CD zymogen (free of any interfering side activity) is for example very suitable for determining low FIXa concentrations in aqueous solutions, preferably in body fluids such as blood or plasma. FIXa activates the inactive rFX-EGF2-AP-CD zymogen by cleavage. The zymogen activation is measured by a coupled indicator region using a chromogenic FXa peptide substrate such as e.g. Chromozym X. The FIXa activity to be determined is amplified by the amplification system of the zymogen activation. Such a FIXa test is for example described by Van Dam-Mieras, M. C. E. et al., In: Bergmeyer, H. U. (ed.), Methods of Enzymatic Analysis, Vol. V, page 365–394, 3rd ed., Academic Press, New York (1983).

Test Principle:

| | | | |
|---|---|---|---|
| 1. | | FIXa | |
| | rFX-EGF2-AP-CD | → | rFXa-EGF2-AP-CD |
| | rFXa-EGF2-AP-CD | | |
| 2. | MOC-D-NleGlyArg-pNA | → | MOC-D-NleGlyArg + pNA |
| Measurement signal: | pNA (p-nitroaniline) | | |
| FXa substrate: | MOC-D-NleGlyArg-pNA (Chromozym X) | | |
| Test mixture: | 200 µl buffer | | |
| | + 20 µl rFX-EGF2-AP-CD (0.13 mg/ml; 4 µmol/l) | | |
| | + 25 µl substrate (Chromozym X, 8 mmol/l) | | |
| | + 20 µl FIXa sample | | |
| Buffer: | 50 mmol/l Tris-HCl, pH 8.0, 150 mmol/l NaCl; 5 mol/l CaCl$^2$; 0.1% PEG 8000 | | |

The test mixture was incubated at RT in a microtitre plate and the absorbance was measured at 405 nm against a reagent blank value versus time. The direct conversion of Chromozym X by FIXa is negligible under the given test conditions.

The factor IXa catalysed activation of the zymogen rFX-EGF2-AP-CD is measured using the chromogenic peptide substrate Chromozym X. The formation of p-nitroaniline (measurement signal) is a measure (proportional) of the factor IX activity (to be determined) that is present.

EXAMPLE 15

Crystallization of rFXa-EGF2-AP-CD

The activated purified recombinantly produced rFXa-EGF2-AP-CD protease was dialysed for 6 h at 4° C. against 2×100 vol 5 mmol/l HEPES buffer, pH 6.5 and subsequently concentrated to a concentration of 10 mg/ml in a Centrikon® 10 microconcentrator from the Amicon Company (Witten, GFR). It is crystallized by vapour diffusion in a sitting drop. 4 µl concentrated rFXa-EGF2-AP-CD protease (at an equimolar concentration with the inhibitor H-Glu-Gly-Arg-chloromethylketone (Bachem Biochemica, GmbH, Heidelberg, GFR) was admixed at 4° C. with 4 µl 100 mmol/l Tris-HCl, 5 mmol/l CaCl$_2$, 22% polyethylene glycol 6K (PEG 6K), pH 8.2. and equilibrated at 4° C. against a reservoir of 500 µl 100 mmol/l Tris-HCl, 5 mmol/l CaCl$_2$, 22% PEG 6K, pH 8.2 by vapour diffusion in a sitting drop. Crystals grew after 3 to 7 days.

EXAMPLE 16

Test for Finding PXa Inhibitors

FXa protease inhibitors were identified by inhibition of the FXa activity. For this the FXa activity of the recombinantly produced rFXa-EGF2-AP-CD protease variants was determined in the absence and presence of the substance to be tested or of a substance mixture and the percentage inhibition was calculated by forming the quotient. The inhibition constant Ki was determined from the inhibition kinetics.

Test Principle:

| | |
|---|---|
| | rFXa-EGF2-AP-CD |
| MOC-D-NleGlyArg-pNA | → MOC-D-NleGlyArg + pNA |
| Measurement signal: | pNA (p-nitroaniline) |
| FXa substrate: | MOC-D-NleGlyArg-pNA (Chromozym X) |
| Test mixture: | 200 µl buffer |
| | + 20 µl rFX-EGF2-AP-CD (0.13 mg/ml; 4 µmol/l) |
| | + 25 µl substrate (Chromozym X, 8 mmol/l) |
| | + 20 µl FIXa sample |
| Buffer: | 50 mmol/l Tris-HCl, pH 7.4, 150 mmol/l NaCl; 5 mol/l CaCl$_2$; 0.1% PEG |

The test mixture was incubated at RT in a microtitre plate and the linear initial gradient (ΔA/min) was determined by absorbance measurements at 405 nm.

List of References

Bang, N. U.; Beckmann, R. J.; Jaskunas, S. R.; Lai, M.-H. T.; Little, S. P.; Long, G. L.; Santerre, R. F.: Vectors and methods for expression of human protein C activity. EP 0 191 606.

Bergmeyer, H. U. (ed.): Methods of Enzymatic Analysis, Vol. V, chapter 3, 3rd ed., Academic Press, New York (1983).

Bharadwaj, D.; Harris, R. J.; Kisiel, W.; Smith, K. J.: Enzymatic removal of sialic acid from human factor IX and factor X has no effect on their coagulant activity. J. Biol. Chem. 270, 6537–6542 (1995).

Blow, D. M.: Structure and mechanism of chymotrypsin. Acc. Chem. Res. 9, 145–152 (1976).

Brinkmann, U.; Mattes, R. E.; Buckel, P.: High-level of recombinant genes in *Escherichia coli* is dependent on the availability of the dnaY gene product. Gene 85, 109114 (1989).

Van Dam-Mieras, M. C. E.; Muller, A. D.; van Dieijen, G.; Hemker, H. C.: Blood coagulation factors II, V, VII, VIII, IX, X and XI: Determination with synthetic substrates. In: Bergmeyer, H. U. (ed.): Methods of Enzymatic Analysis, Vol. V, Enzymes 3: Peptidases, Proteinases and Their Inhibitors, page 365–394, 3rd ed., Academic Press, New York (1983).

Davie, E. W.; Fujikawa, K.; Kisiel, W.: The coagulation cascade: Initiation, maintenance, and regulation. Biochem. 30, 10363–10379 (1991).

DiBella, E. E.; Maurer, M. C.; Scheraga, H. A.: Expression and folding of recombinant bovine prethrombin-2 and its activation to thrombin. J. Biol. Chem. 270, 163–169 (1995).

Esmon, C. T., Prothrombin activation, doctoral dissertation, Washington University, St. Louis, Mo. (1973).

Fujikawa, K.; Legaz, M. E.; Davie, E. W.: Bovine factor XI (Stuart factor). Mechanism of activation by a protein from Russell's viper venom. Biochem. 11, 4892–4898 (1972).

Furie, B.; Furie, B. C.: The molecular basis of blood coagulation. Cell 53, 505–518 (1988).

Grodberg, J.; Dunn, J. J.: OmpT encodes the *Escherichia coli* outer membrane protease that cleaves T7 RNA polymerase during purification. J. Bacteriol. 170, 1245–1253 (1988).

Hagen, F. S.; Murray, M. J.; Busby, S. J.; Berkner, K. L.; Insley, M. Y.; Woodbury, R. G.; Gray, C. L.: Expression of factor VII activity in mammalian cells. EP 0 200 421.

Hertzberg, M. S.; Ben-Tal, O.; Furie, B.; Furie, B. C.: Construction, expression, and characterization of a chimera of factor IX and factor X. J. Biol. Chem. 267, 14759–14766 (1992).

Holly, R. D.; Foster, D. C.: Methods for producing thrombin. WO 93/13208.

Kaul, R. K.; Hildebrand, B.; Roberts, S.; Jagadeeswaran, P.: Isolation and characterization of human blood-coagulation factor X cDNA. Gene 41, 311–314 (1986).

Kopetzki, E.; Rudolph, R.; Grossmann, A.: Recombinant corestreptavidin. WO 93/09144.

Laemmli, U. K.: Cleavage of structural proteins during the assembly of the head of bacteriophage T4. Nature 227, 680–685 (1970).

Lin, S.-W.; Smith, K. J.; Welsch, D.; Stafford, D. W.: Expression and characterization of human factor IX and factor IX-factor X chimeras in mouse C127 cells. J. Biol. Chem. 265, 144–150 (1990).

McGraw, R. A.; Davis, L. M.; Noyes, C. M.; Lundblad, R. L.; Roberts, H. R.; Graham, J. B.; Stafford, D. W.: Evidence for a prevalent dimorphism in the activation peptide of human coagulation factor IX. Proc. Natl. Acad. Sci. USA 82, 2847–2851 (1985).

Medved, L. V.; Orthner, C. L.; Lubon, H.; Lee, T. K.; Drohan, W. N.; Ingham, K. C.: Thermal stability and domain-domain interactions in natural and recombinant protein C. J. Biol. Chem. 270, 13652–13659 (1995).

Mullis, K. B.; Faloona, F. A.: Specific synthesis of DNA in vitro via a polymerase-catalyzed chain reaction. Methods Enzymol. 155, 355–350 (1987).

Nicolaisen, E. M.; Bjorn, S. E.; Wiberg, F. C.; Woodbury, R.: Modified factor VII/VIIa. WO 88/10295

Pedersen, A. H.; Lund-Hansen, T.; Bisgaard-Frantzen, H.; Olsen, F.; Petersen, L. C.: Autoactivation of human recombinant coagulation factor VII. Biochem. 28, 9391–9336 (1989).

Polgar, L.: Structure and function of serine proteases. In: Mechanisms of protein action. Boca Raton, Fla., CRC Press, chapter 3 (1989).

Rezaie, A. R.; Neuenschwander, P. F.; Morrissey, J. H.; Esmon, C. T.: Analysis of the functions of the first epidermal growth factor-like domain of factor X. J. Biol. Chem. 268, 8176–8180 (1993).

Rezaie, A. R.; Esmon, C. T.: Asp-70-Lys mutant of factor X lacks high affinity $Ca^{2+}$ binding site yet retains function. J. Biol. Chem. 269; 21495–21499 (1994).

Sambrook, J.; Fritsch, E. F.; Maiiiatis, T.: Molecular cloning: A laboratory manual. Cold Spring Harbor Press, Cold Spring Harbor, N.Y., (1989).

Sheehan, J. P.; Wu, Q.; Tollefsen, D. M.; Sadler, J. E.: Mutagenesis of thrombin selectively modulates inhibition by serpins heparin cofactor II and antithrombin III. J. Biol. Chem. 268, 3639–3645 (1993).

Thogersen, H. C.; Holtet, T. L.; Etzerodt, M.: Improved method for the refolding of proteins. WO 94/18227.

Wolf, D. L.; Sinha, U.; Hancock, T. E.; Lin, P.-H.; Messier, T. L.; Esmon, C. T.; Church, W. R.: Design of constructs for the expression of biologically active recombinant human factor X and Xa. J. Biol. Chem. 266, 13726–13730 (1991).

Yee, J.; Rezaie, A. R.; Esmon, C. T.: Glycosaminoglycan contributions to both protein C activation and thrombin inhibition involve a common arginine-rich site in thrombin that includes residues arginine 93, 97, and 101. J. Biol. Chem. 269, 17965–17970 (1994).

Zhong, D. G.; Smith, K. J.; Birktoft, J. J.; Bajaj, S. P.: First epidermal growth factor-like domain of human blood coagulation factor IX is required for its activation by factor VIIa tissue factor but not by factor XIa. Proc. Natl. Acad. Sci. USA 91, 3574–3578 (1994).

What is claimed is:

1. An isolated, non-glycosylated, enzymatically active protein with serine protease activity or a zymogenic form thereof consisting of the following domains of a member of the factor IX family:

(a) at least one of either an EGF1 or EGF2 domain, linked by its C-teiminus to, (b) the N-teiminus of a zymogen activation domain, which is linked by its C-teirminus to, (c) the N-teiminus of a catalytic domain.

2. The isolated protein of claim 1, wherein (a) is an EGF1 domain.

3. The isolated protein of claim 1, wherein (a) is an EGF2 domain.

4. The isolated protein of claim 1, wherein (a) consists of an EGF 1 domain linked by its C-terminus to the N-teiminus of an EGF2 domain.

5. The isolated protein of claim 1 wherein at least one of (a), (b), and (c), is from a member of the factor IX family which differs from the family from which the other domains are from.

6. The isolated protein of claim 1, wherein each of (a), (b), and (c) is from a different member of the factor IX family.

7. The isolated protein of claim 1, wherein said EGF2 domain and said catalytic domain are from factor X, and said zymogen activation domain is from factor IX.

8. The isolated protein of claim 1 wherein (a), (b), and (c), are from either factor IX or factor X.

9. The isolated protein of claim 8, wherein at least one of (a), (b), and (c) is from factor IX, and the remaining domains are from factor X.

10. The isolated protein of claim 8, wherein at least one of (a), (b), and (c) is from factor X, and the remaining domains are from factor IX.

11. A process for the manufacture of the protein of claim 1, comprising transforming a prokaryotic cell with an expression vector that encodes said protein and culturing the transfoimed prokaiyotic cell under conditions favoring production of said protein.

12. A method for determining if a substance is an inhibitor or activator of a member of the factor IX family, comprising contacting said substance with the isolated protein of claim 1, and determining activity of said protein, wherein a change in said activity, relative to said activity prior to said contact is indicative of activator or inhibitor properties of said substance.

13. A method for the determination of factor IXa in a sample comprising incubating a zymogenic form of the protein of claim 1 with a substrate cleavable by an active form of said zymogen, wherein determining cleavage of said substrate is indicative of factor IXa in a sample.

14. The method of claim 13, wherein said sample is a body fluid.

15. The method of claim 13, wherein said cleavable substrate is a chromogenic substrate.

16. The method of claim 13, wherein the cleavable substrate is a second zymogenic form of an enzyme activatable by the active form of the protein of claim 1, which is activatable by the factor IXa.

17. An isolated, non-glycosylated, enzymatically active protein with serine protease activity or a zymogenic form thereof, consisting of an amino acid sequence encoded by nucleotides 322 to 462 of SEQ ID NO: 15, concatenated to an amino acid sequence encoded by nucleotides 535 to 1005 of the nucleotide sequence set forth in SEQ ID NO: 16, concatenated to an amino acid sequence encoded by nucleotides 964 to 1362 as set forth in SEQ ID NO: 15.

\* \* \* \* \*